United States Patent
Pang et al.

(10) Patent No.: US 12,269,788 B2
(45) Date of Patent: *Apr. 8, 2025

(54) COMPOSITION FOR REMOVING POLYMER

(71) Applicant: Dongwoo Fine-Chem Co., Ltd., Jeollabuk-do (KR)

(72) Inventors: Soon-Hong Pang, Jeollabuk-do (KR); Kyeong-Muk Choi, Jeollabuk-do (KR); Han-Byeol Kang, Gyeonggi-do (KR)

(73) Assignee: DONGWOO FINE-CHEM CO., LTD. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/215,038

(22) Filed: Jun. 27, 2023

(65) Prior Publication Data

US 2023/0339843 A1 Oct. 26, 2023

Related U.S. Application Data

(63) Continuation of application No. 17/198,184, filed on Mar. 10, 2021, now Pat. No. 11,739,048.

(30) Foreign Application Priority Data

Mar. 26, 2020 (KR) .................. 10-2020-0036615

(51) Int. Cl.
| | | |
|---|---|---|
| C11D 3/24 | (2006.01) | |
| C07C 211/63 | (2006.01) | |
| C07C 211/64 | (2006.01) | |
| C09J 183/04 | (2006.01) | |
| C11D 3/28 | (2006.01) | |
| C11D 3/30 | (2006.01) | |
| C11D 3/34 | (2006.01) | |
| C11D 3/43 | (2006.01) | |
| C11D 3/44 | (2006.01) | |
| H01L 21/02 | (2006.01) | |

(52) U.S. Cl.
CPC .......... *C07C 211/64* (2013.01); *C07C 211/63* (2013.01); *C09J 183/04* (2013.01); *C11D 3/245* (2013.01); *C11D 3/28* (2013.01); *C11D 3/30* (2013.01); *C11D 3/3445* (2013.01); *C11D 3/43* (2013.01); *H01L 21/02082* (2013.01); *C09J 2301/502* (2020.08); *C11D 2111/22* (2024.01)

(58) Field of Classification Search
CPC .... C11D 3/28; C11D 3/30; C11D 3/43; C11D 3/3445
USPC ....... 510/175, 176, 492, 499, 500, 501, 505, 510/506
See application file for complete search history.

(56) References Cited

U.S. PATENT DOCUMENTS

| | | | |
|---|---|---|---|
| 6,652,665 B1 | 11/2003 | Sachdev et al. | |
| 7,192,910 B2 | 3/2007 | Wojtczak et al. | |
| 11,739,048 B2 * | 8/2023 | Pang | C11D 3/3445 |
| | | | 156/247 |
| 2009/0093107 A1 | 4/2009 | Lee et al. | |
| 2010/0163788 A1 | 7/2010 | Visintin et al. | |

FOREIGN PATENT DOCUMENTS

| | | | | |
|---|---|---|---|---|
| CA | 2544209 | | 5/2005 | |
| EP | 1975987 A2 | * | 10/2008 | ............. C11D 1/004 |
| JP | 2009-194087 | | 8/2009 | |
| KR | 2003-0093974 | | 12/2003 | |
| KR | 10-2009-0096728 | | 9/2009 | |
| KR | 10-2014-0060389 | | 5/2014 | |
| KR | 10-2015-0016430 | | 2/2015 | |
| KR | 10-2016-0039945 | | 4/2016 | |
| KR | 10-2016-0073288 | | 6/2016 | |
| WO | WO-2007120259 A2 | * | 10/2007 | ......... C11D 11/0047 |
| WO | WO-2008080097 A2 | * | 7/2008 | ............. C09K 13/00 |
| WO | WO-2008157345 A2 | * | 12/2008 | ............. C09K 13/08 |
| WO | WO-2010039936 A2 | * | 4/2010 | ............. C09K 13/08 |

* cited by examiner

*Primary Examiner* — Gregory R Delcotto
(74) *Attorney, Agent, or Firm* — Wells St. John P.S.

(57) ABSTRACT

Disclosed is a composition for removing polymers. The composition contains a fluorinated alkyl compound, a polar aprotic solvent, and an acyclic secondary or tertiary amine compound.

6 Claims, No Drawings

COMPOSITION FOR REMOVING POLYMER

CROSS REFERENCE TO RELATED APPLICATION(S)

This patent claims priority to U.S. patent application Ser. No. 17/198,184, filed Mar. 10, 2021, which claims priority to and the benefit of Korean Patent Application No. 10-2020-0036615, filed Mar. 26, 2020, each of which is hereby incorporated by reference in its entirety into this application.

BACKGROUND OF THE INVENTION

1. Technical Field

The present invention relates to a composition for removing a silicone polymer.

2. Description of the Related Art

When manufacturing semiconductor devices, after electronic circuits or the like are formed on the front surface (hereinafter, referred to as "circuitry surface") of a semiconductor wafer (hereinafter, simply referred to as "wafer"), there are cases where back grinding, which is the process of grinding the back surface of the wafer, is performed to decrease the thickness of the wafer. In this case, in order to protect the circuitry surface of the wafer or to prevent the wafer from moving, a support is usually attached to the circuitry surface of the wafer via an adhesive polymer (for example, silicone polymer). The support attached to the circuitry surface of the wafer has the advantages of reinforcing the wafer that is thinned through the back grinding and of allowing back electrodes or the like to be formed on the ground back surface of the wafer.

After the back grinding and the formation of the back electrodes are performed, the support is removed from the circuitry surface of the wafer, the adhesive polymer is peeled off, and the wafer is subject to dicing to produce semiconductor chips.

In recent years, a chip stacking technique using through-electrodes (for example, silicon through-electrodes) that are electrodes formed to extend through a wafer has been developed and used. According to the chip stacking technique, since electronic circuits of multiple chips are electrically connected by through-electrodes instead of typical wires, it is possible to achieve high density integration and high speed operation of electronic circuits. When this chip stacking technique is used, the back grinding is often performed to reduce the thickness of an assembly in which a plurality of chips is stacked. Therefore, usage of a support and an adhesive polymer is increasing.

With regard to this matter, a support is usually attached to the circuitry surface of a wafer by an adhesive polymer and the adhesive polymer is then thermally cured to securely attach the support to the wafer. Therefore, when the adhesive polymer is peeled off, the cured adhesive polymer is likely to remain on the circuitry surface of the wafer. Therefore, there is a need for a means for efficiently removing the cured adhesive polymer remaining on the circuitry surface of the wafer. In addition, when the adhesive polymer is removed, there is a problem in that metal films or bump balls are likely to be damaged due to metal corrosion.

Patent Document 1 discloses a composition for removing adhesive polymers. However, this composition has a problem in that the removal rate is slow for reticulated polymers.

Document of Related Art

Patent Document (Patent Document 1) Korean Patent Application Publication No. 10-2014-0060389

SUMMARY OF THE INVENTION

The present invention has been made to address the problems occurring in the related art described above, and an objective of the present invention is to provide a composition for removing a polymer, the composition being capable of efficiently and quickly removing an adhesive polymer remaining on a circuitry surface of a wafer during a semiconductor device manufacturing process without causing metal corrosion.

The effects, features, and objectives of the present invention are not limited to the ones mentioned above, and other effects, features, and objectives not mentioned above can be clearly understood by the ordinarily skilled in the art from the following description.

In order to achieve the objective of the present invention, there is provided a composition for removing a polymer, the composition including a fluorinated alkyl compound, a polar aprotic solvent, and an amine compound. The amine compound includes an acyclic secondary amine compound or an acyclic tertiary amine compound.

According to the present invention, there is provided a polymer removing composition capable of improving a polymer removal rate by including an acyclic secondary or tertiary amine. The polymer removing composition of the present invention, in particular, can remove a silicone-based polymer at high speed and can minimize damage to metal films or bump balls by preventing metal corrosion.

DESCRIPTION OF THE PREFERRED EMBODIMENTS

The present invention relates to a polymer removing composition containing a fluorine compound, a solvent, and an amine compound. The fluorine compound is a fluorinated alkyl compound, the solvent is a polar aprotic solvent, and the amine compound is an acyclic secondary amine compound or an acyclic tertiary amine compound.

In the present invention, the alkyl group refers to a hydrocarbon group combined with a single bond.

<Composition for Removing Polymer>

According to the present invention, a composition for removing a polymer contains a fluorinated alkyl compound, a polar aprotic solvent, and an amine compound. The composition may further contain other additives and may be used to remove silicone polymers.

The polymers to be removed with the composition are not particularly limited but are preferably silicone polymers. Specifically, the silicone polymers include linear polymers and reticulated polymers. For example, the silicone polymers include a polyorganosiloxane-based resin that forms a reticulated polymer through curing as well as a linear non-reactive polydimethylsiloxane polymer.

In particular, the composition of the present invention has an advantage of removing not only linear polymers but also reticulated polymers because the fluorinated alkyl compound decomposes and dissolves silicone polymers.

According to the present invention, since the amine compound adjusts the pH of the composition to an appropriate level, the effect of preventing metal corrosion during polymer removal can be obtained. Thus, damage to metal films or bump balls can be prevented. Specifically, the composition can protect metals such as Sn, Sn/Ag alloy, and Sn/Au alloy by preventing metal corrosion. In this case, the metals that can be protected are not limited thereto.

In addition, the polymer removing composition according to the present invention does not contain water that is intentionally added. It is preferable that the polymer removing composition does not contain water. However, if necessary, a hydrate of a fluorinated alkyl compound may be used. In this case, the polymer removing composition may contain a small amount of water. In this case, the water may be contained in the composition in an amount of less than 4% by weight with respect to the total weight of the composition. When the content of water exceeds that range, polymer removability decreases and metal corrosion increases.

In addition, it is preferable that the polymer removing composition according to the present invention does not contain a compound having a hydroxide (—OH) group, for example, an alcohol-based compound in the molecular structure thereof. In the case where a compound has a hydroxide group in the molecular structure thereof, there is a problem in that the hydroxide group inhibits the activity of a fluorine compound, thereby deteriorating the removability of silicone resin.

(A) Fluorinated Alkyl Compound

The polymer removing composition according to the present invention contains a fluorinated alkyl compound. The fluorinated alkyl compound serves to reduce the molecular weight by breaking the ring of a polymer (for example, silicone polymer).

In the present invention, an example of the fluorinated alkyl compound is an alkyl ammonium fluoride. Specifically, examples of the fluorinated alkyl compound include one or more compounds represented by Formula 4-1 or Formula 4-2.

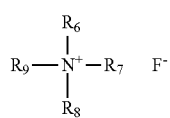

[Formula 4-1]

In Formula 4-1, $R_6$ to $R_9$ each are an alkyl group having three to ten carbon atoms (C3 to C10). When $R_6$ to $R_9$ each is an alkyl group having two or less carbon atoms (C2 or below), since the solubility of the fluorine compound in the solvent is lowered, a precipitate occurs immediately after mixing or occurs when a certain period of time elapses after mixing.

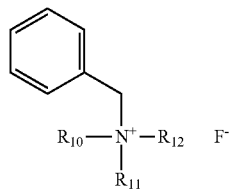

[Formula 4-2]

In Formula 4-2, $R_{10}$ to $R_{12}$ each are an alkyl group having one to ten carbon atoms (C1 to C10).

For example, as the fluorinated alkyl compound, one or more compounds selected from among tetrabutylammonium bifluoride (TBAF HF), tetrabutylammonium fluoride (TBAF), tetraoctylammonium fluoride (TOAF), and benzyltrimethylammonium fluoride (BTMAF) are used singly or in combination.

When the alkyl ammonium fluoride is present in the form of a hydrate, examples of the alkyl ammonium fluoride include tetra-n-butylammonium fluoride hydrate, tetra-n-butylammonium fluoride trihydrate, benzyltrimethylammonium fluoride hydrate, and the like.

The fluorinated alkyl compound is contained in an amount of 0.1 to 20% by weight and preferably 0.5 to 17% by weight with respect to the total weight of the polymer removing composition. When the fluorine compound is contained in an amount of less than 0.1% by weight, there is a problem in that the polymer (silicone resin) attached to electronic components cannot be effectively removed. On the other hand, when the fluorine compound is contained in an amount of 20% by weight or more and it is present in the form of a hydrate-type alkyl ammonium fluoride, the water content is increased, thereby deteriorating the effect of removing a polymer such as silicone resin. In addition, metal films are corroded due to an excessive amount of fluoride.

(B) Polar Aprotic Solvent

The polymer removing composition according to the present invention contains a polar aprotic solvent. The polar aprotic solvent swells a silicone polymer and dissolves the fluorine compound and the decomposed silicone polymer.

Water and alcohol-based compounds (for example, diethylene glycol nomomethyl ether, ethylene glycol, isopropyl alcohol, etc.), which are generally known solvents, are difficult to remove polymers due to hydrogen bonding with fluorine ions. Therefore, it is preferable that the solvent in the polymer removing composition according to the present invention does not include water or an alcohol-based compound.

The polar aprotic solvent includes at least one solvent selected from the group consisting of ketone-based, acetate-based, amide-based, pyridine-based, morpholine-based, pyrrolidone-based, urea-based, phosphate-based, sulfoxide-based, nitrile-based, carbonate-based, oxazolidone-based, and piperazine-based solvents.

Specifically, examples of the ketone-based solvent include compounds represented by Formula 5-1:

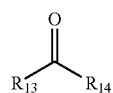

[Formula 5-1]

In Formula 5-1, $R_{13}$ and $R_{14}$ each are independently a linear or branched aliphatic hydrocarbon having 1 to 18 carbon atoms (C1 to C18), and the sum of the numbers of carbon atoms of $R_{13}$ and $R_{14}$ is preferably 2 or more and less than 30.

Examples of the ketone solvent include 2-heptanone, 3-heptanone, 4-heptanone, 3-pentanone, 2-hexanone, 3-hexanone, 4-methyl-2-pentanone, 5-methyl-2-hexanone, and 2,6-dimethyl-4-hexanone but are not limited thereto.

Specifically, examples of the acetate-based solvent include methyl acetate, ethyl acetate (EA), propyl acetate, isopropyl acetate, N-butyl acetate, isobutyl acetate, sec-butyl acetate, amyl acetate, pentyl acetate, Isopentyl acetate, octyl acetate, benzyl acetate, phenyl acetate, ethoxyethyl acetate, methoxybutyl acetate (MBA), propylene glycol monomethyl ether acetate (PGMEA), vinyl acetate, or ethyl ethoxypropionate (EEP), and the like but are not limited thereto.

Specifically, examples of the amide-based solvent include N,N-dimethylacetamide, N,N-diethylacetamide, N,N-dipropylacetamide, N-ethyl-N-methylacetamide, N,N-dimethylpropionamide, N,N-dimethylbutyramide, N,N-dimethylisobutyramide, N,N-dimethylpentanamide, N,N-dimethylpropanamide, N,N-diethylpropanamide, and N,N-dibutylpropanamide but are not limited thereto.

Specifically, examples of the pyridine-based solvent include compounds represented by Formula 5-2:

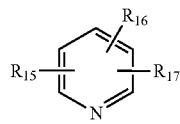

[Formula 5-2]

In Formula 5-2, $R_{15}$ to $R_{17}$ each are independently hydrogen, a linear or branched aliphatic hydrocarbon group having one to ten carbon atoms (C1 to C10), a halogen (for example, F, Cl, Br, I), an aldehyde group (—CHO), an acetaldehyde group (—COCH3), an alkoxy group having one to four carbon atoms (C1 to C4), a vinyl group, an acetylene group, a cyano group (—CN), or a methyl sulfide group (—SCH3).

Examples of the pyridine solvent include pyridine, 2-methylpyridine, 3-methylpyridine, 4-methylpyridine, 4-ethylpyridine, 4-propylpyridine, 4-isopropylpyridine, 4-amylpyridine, 2, 3-lutidine, 2,4-lutidine, 2,5-lutidine, 3,4-lutidine, 3,5-lutidine, and 2,4,6-trimethylpyridine but are not limited thereto.

Specifically, examples of the morpholine solvent include compounds represented by Formula 5-3:

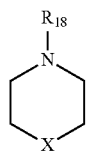

[Formula 5-3]

In Formula 5-3, $R_{18}$ is hydrogen, a linear or branched aliphatic hydrocarbon group having one to six carbon atoms (C1 to C6), a vinyl group, a cyano group (—CN), an aliphatic hydrocarbon group having one to four carbon atoms (C1 to C4) and being substituted by a tertiary amine, or a phenyl or pyridine group substituted by an alkyl group having one to four carbon atoms (C1 to C4), a cyano group (—CN), a halogen group (for example, F, Cl, Br, or I) or an aldehyde group (—CHO); X is oxygen or —NR19-; and $R_{19}$ is an aliphatic hydrocarbon group having one to four carbon atoms (C1 to C4).

Examples of the morpholine-based solvent include N-methylmorpholine, N-ethylmorpholine, N-arylmorpholine, N-butylmorpholine, N-isobutylmorpholine, and the like but are not limited thereto.

Specifically, examples of the pyrrolidone-based solvent include N-methylpyrrolidone (NMP), N-ethylpyrrolidone (NEP), and N-vinylpyrrolidone (NVP) but are not limited thereto.

Specifically, examples of the urea-based solvent include compounds represented by Formula 5-4:

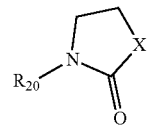

[Formula 5-4]

In Formula 5-4, X is oxygen or —NR19-, and $R_{19}$ and $R_{20}$ each are independently a linear, branched or cyclic aliphatic hydrocarbon group having one to six carbon atoms (C1 to C6) or an aliphatic hydrocarbon group having one to four carbon atoms (C1 to C4) and being substituted by a vinyl group, a phenyl group, an acetylene group, a methoxy group, or a dimethylamino group.

Examples of the urea-based solvent include tetramethylurea, tetraethylurea, tetrabutylurea, and the like but are not limited thereto.

Specifically, examples of the phosphate-based solvent include compounds represented by Formula 5-5:

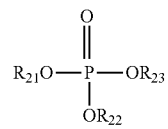

[Formula 5-5]

In Formula 5-5, $R_{21}$ to $R_{23}$ each are independently a linear or branched aliphatic hydrocarbon group having one to eight carbon atoms (C1 to C8), a divalent aliphatic hydrocarbon group having three to eight carbon atoms (C3 to C8) and forming a ring with an adjacent oxygen, a phenyl group unsubstituted or substituted by an aliphatic hydrocarbon group having one to four carbon atoms (C1 to C4), an aliphatic hydrocarbon group having two to four carbon atoms and being substituted by a halogen (for example, F, Cl, Br, or I), or a phenyl group substituted by a halogen. The group "—CH2-" contained in the linear or branched aliphatic hydrocarbon group having one to eight carbon atoms (C1 to C8) can be substituted with an oxygen atom.

Examples of the phosphate-based solvent include triethyl phosphate, tributyl phosphate, triamyl phosphate, triaryl phosphate and the like but are not limited thereto.

Specifically, examples of the sulfoxide-based solvent include dimethyl sulfoxide (DMSO), dibutyl sulfoxide, diphenyl sulfoxide, dibenzyl sulfoxide, and methylphenyl sulfoxide but are not limited thereto.

Specifically, examples of the nitrile-based solvent include propionitrile, butyronitrile, isobutyronitrile, acetonitrile, trimethylacetonitrile, and phenylacetonitrile but are not limited thereto.

Specifically, examples of the carbonate-based solvent include dimethyl carbonate (DMC), diethyl carbonate, diphenyl carbonate, dibenzyl carbonate, ethylene carbonate, propylene carbonate (PC), and vinylene carbonate but are not limited thereto.

Specifically, examples of the oxazolidone-based solvent include 2-oxazolidone, 3-methyl-2-oxazolidone, and the like but are not limited thereto.

Examples of the piperazine-based solvent include dimethyl piperazine, dibutyl piperazine, and the like but are not limited thereto.

On the other hand, according to the present invention, the polar aprotic solvent does not include an acyclic tertiary amine to be described later.

The polar aprotic solvent is contained in an amount of 60 to 99.89% by weight and preferably 68 to 99.45% by weight with respect to the total weight of the polymer removing composition. When the polar aprotic solvent is contained in an amount of less than 60% by weight, there is a problem in that metal films are corroded. On the other hand, when the content of the polar aprotic solvent exceeds 99.89% by weight, there is a problem in that silicone resin attached to electronic components cannot be effectively removed.

(C) Amine Compound

The polymer removing composition according to the present invention contains an amine compound, and the amine compound is an acyclic secondary amine compound or an acyclic tertiary amine compound. The amine compound promotes the swelling of a silicone polymer and improves the solubility of a fluorinated alkyl compound, thereby improving the removal rate of the silicone polymer. In the present invention, the amine compound exhibits an anti-corrosion effect by adjusting the pH of the polymer removing composition to an appropriate level.

In terms of maximizing the functional effects of the amine compound in the polymer removing composition, an amine compound having a specific structure is suitably used. For example, the effect of swelling a silicone polymer is enhanced when the number of carbon atoms in the alkyl group of the amine is increased, and the effect of improving the solubility of the fluorinated alkyl compound is enhanced when the number of carbon atoms in the alkyl group of the amine is decreased. In addition, the better the ionization of the fluorinated alkyl compound is, the more corrosion occurs. In order to obtain the complementary effect, the amine compound is used. That is, the amine compound improves the removal of a polymer and alleviates the corrosion of metal. Specifically, an amine compound having a specific structure described below is preferably used.

Specifically, examples of the amine compound used in the present invention include compounds represented by any one of Formulas 1 to 3.

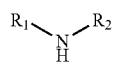

[Formula 1]

In Formula 1, $R_1$ and $R_2$ each independently represent a linear or branched alkyl group having one to eight carbon atoms (C1 to C8). When $R_1$ and $R_2$ are the same, $R_1$ and $R_2$ preferably represent an alkyl group having four or more carbon atoms.

More preferably, $R_1$ and $R_2$ each independently represent a linear or branched alkyl group having two to eight carbon atoms (C2 to C8). When $R_1$ and $R_2$ are the same, $R_1$ and $R_2$ preferably represent a linear or branched alkyl group having four to eight carbon atoms (C4 to C8).

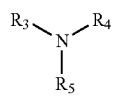

[Formula 2]

In Formula 2, $R_3$ to $R_5$ each represent an alkyl group having one to eight carbon atoms (C1 to C8).

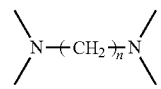

[Formula 3]

In Formula 3, n is a positive integer among 3, 4, 5, and 6.

The amine compound is preferably an amine compound having a boiling point of 140° C. or higher and more preferably an amine compound having a boiling point in a range of 140° C. to 300° C. When the amine compound satisfies one of Formulas 1 to 3 and has a boiling point of 140° C. or higher, since volatile components are minimized, the polymer removing composition according to the present invention can be easily applied to a device manufacturing process. When the amine compound has a boiling point of 140° C. or higher, it is possible to expect not only the effect of improving the polymer removal performance but also the effect of preventing metal corrosion. When the amine compound has a boiling point lower than 140° C., a considerable improvement in polymer removal performance is expected but the effect of preventing corrosion of metals is insignificant. Thus, it is difficult to obtain both the effect of improving polymer removal performance and the effect of preventing metal corrosion.

For example, the amine compound includes one or more compounds selected from the group consisting of tripropylamine (having a boiling point of 158° C.), tributylamine (having a boiling point of 215° C.), tripentylamine (having a boiling point of 242° C.), triisobutylamine (having a boiling point of 191° C.), dimethyloctylamine (having a boiling point of 192° C.), diethylbutylamine (having a boiling point of 141° C.), diisobutylamine (having a boiling point of 141° C.), N,N,N',N'-tetramethyl-1,3-diaminopropane (having a boiling point of 144° C.), N,N,N',N'-tetramethyl-1,4-diaminobutane (having a boiling point of 169° C.), and N,N,N',N'-tetramethyl-1,6-diaminohexane (having a boiling point of 209° C.).

The amine compound is contained in an amount of 0.01 to 20% by weight and preferably 0.05 to 15% by weight with respect to the total weight of the polymer removing composition. When the amine compound is contained in an amount of less than 0.01%, it is difficult to expect an improvement in removal rate. On the other hand, when the content of the amine compound exceeds 20% by weight, the polymer swelling effect does not increase in proportion to the amount of the amine compound that is contained, and metal corrosion increases.

(D) Additives

In addition to the components described above, the polymer removing composition according to the present invention optionally contain additional components such as corrosion inhibitors and surfactants commonly used in this field.

The corrosion inhibitor is used to effectively suppress corrosion of a metal-containing underlying film during removal of a resin. The corrosion inhibitor is commercially available from various sources and may be used without further purification.

The surfactant is used to enhance the effect of removing polymers. For example, anionic surfactants, cationic surfactants, and nonionic surfactants may be used. Among them, it is preferable to use a nonionic surfactant having excellent wettability and generating a few bubbles. One or more surfactants selected from those surfactants may be used singly or in combination.

The present invention also provides a method for removing a polymer from a device using the polymer removing composition according to the present invention. All the details that have been described in connection with the polymer removing composition according to the present invention can be applied to the polymer removal method according to the present invention. Hereinbelow, although the redundant detailed descriptions will not be given, the same can be applied to the polymer removing method according to the present invention.

Specifically, the polymer removal method is a method for removing a polymer such as a silicon adhesive used in a wafer thinning process. The wafer thinning process includes a step of forming a silicone release layer and a silicone adhesive layer between a carrier wafer and a device wafer and a step of thinning the device water. The silicone release layer serves as a separation location at which the carrier wafer is removed while not causing damage to the device wafer. The silicone adhesive bonds the device wafer to the carrier wafer and undergoes a curing process. After such a process, the cured polymer is removed with the use of the polymer removing composition according to the present invention.

The present invention will be described in more detail with reference to examples described below. The examples are intended to describe the present invention in more detail but the scope of the present invention is not limited to the examples.

Examples and Comparative Examples: Preparation of Polymer Removing Composition

Polymer removing compositions were prepared according to components and composition ratios listed in Tables 1 and 2.

TABLE 1

| Unit: wt % | (A) Fluorine compound | | (B) Solvent | | (C) Amine compound | |
| --- | --- | --- | --- | --- | --- | --- |
|  | Kind | Content | Kind | Content | Kind | Content |
| Example 1 | A-1 | 5 | B-1 | 90 | C-1 | 5 |
| Example 2 | A-2 | 5 | B-2 | 85 | C-2 | 10 |
| Example 3 | A-2 | 6 | B-3 | 91 | C-3 | 3 |
| Example 4 | A-3 | 4 | B-4 | 84 | C-3 | 10 |
| Example 5 | A-2 | 5 | B-4 | 90 | C-3 | 5 |
| Example 6 | A-2 | 7 | B-5 | 92 | C-4 | 1 |
| Example 7 | A-2 | 7 | B-6/B-7 | 40/52.5 | C-5 | 0.5 |
| Example 8 | A-1 | 4 | B-8 | 94 | C-4 | 2 |
| Example 9 | A-1 | 4 | B-9 | 95 | C-1 | 1 |
| Example 10 | A-2 | 1 | B-2 | 99 | C-2 | 2 |
| Example 11 | A-3 | 15 | B-2 | 85 | C-2 | 2 |
| Example 12 | A-2 | 0.5 | B-2 | 99.5 | C-2 | 2 |
| Example 13 | A-2 | 17 | B-2 | 83 | C-2 | 2 |
| Example 14 | A-2 | 6 | B-3 | 79 | C-3 | 20 |
| Example 15 | A-2 | 6 | B-3 | 93.99 | C-3 | 0.01 |
| Example 16 | A-2 | 6 | B-3 | 93.95 | C-3 | 0.05 |
| Example 17 | A-1 | 5 | B-6/B-3 | 50/44 | C-3 | 1 |
| Example 18 | A-2 | 8 | B-10 | 88 | C-2 | 4 |
| Example 19 | A-2 | 8 | B-11 | 77 | C-2 | 15 |
| Example 20 | A-2 | 8 | B-3 | 67 | C-3 | 25 |
| Example 21 | A-1 | 5 | B-4 | 90 | C-6 | 5 |

TABLE 2

| Unit: wt % | (A) Fluorine compound | | (B) Solvent | | (C) Amine compound | |
| --- | --- | --- | --- | --- | --- | --- |
|  | Kind | Content | Kind | Content | Kind | Content |
| Comparative Example 1 | — | — | B-1 | 100 | — | — |
| Comparative Example 2 | — | — | B-5 | 100 | — | — |
| Comparative Example 3 | A-20 | 5 | B-3 | 95 | — | — |
| Comparative Example 4 | A-2 | 5 | B-7 | 95 | — | — |
| Comparative Example 5 | A-2 | 5 | B-22 | 85 | C-1 | 10 |
| Comparative Example 6 | A-2 | 5 | B-23 | 85 | C-1 | 10 |
| Comparative Example 7 | A-1 | 6 | B-2 | 89 | C-20 | 5 |
| Comparative Example 8 | A-1 | 7 | B-20 | 88 | C-1 | 5 |
| Comparative Example 9 | A-2 | 5 | B-21 | 90 | C-1 | 5 |
| Comparative Example 10 | A-1 | 5 | B-4 | 85 | C-21 | 10 |
| Comparative Example 11 | A-1 | 5 | B-4 | 85 | C-22 | 10 |
| Comparative Example 12 | A-1 | 5 | B-4 | 85 | C-23 | 10 |
| Comparative Example 13 | A-1 | 5 | B-1 | 90 | C-24 | 5 |
| Comparative Example 14 | A-1 | 5 | B-1 | 90 | C-25 | 5 |

<Fluorine compound>
A-1 TBAF·HF: tetrabutylammonium bifluoride;
A-2 TBAF: tetrabutylammonium fluoride;
(A-3) BTMAF: benzyltetramethylammonium fluoride;
A-20 ammonium fluoride ($NH_4HF_2$)
<Solvent>
B-1 2-heptanone;
B-2 N,N-diethylacetamide;
B-3 N,N-dimethylpropanamide;
B-4 N-ethylpyrrolidone;
B-5 N-methylmorpholine;
(B-6) N-butyl acetate;
B-7 PGMEA: propylene glycol monomethyl ether acetate;
(B-8) 4-methylpyridine;
(B-9) dimethylpiperazine;
(B-10) triethylphosphate;
(B-11) tetraethylurea;
B-20 ethylene glycol;
B-21 isopropyl alcohol
B-22 water;
B-23 diethylene glycol monomethyl ether
<Amine compound>
C-1 tripropylamine (boiling point 158° C.);
(C-2) diisobutylamine (boiling point 141° C.);
(C-3) tributylamine (boiling point 215° C.);
(C-4) dimethyloctylamine (boiling point 192° C.);
(C-5) N,N,N',N'-tetramethyl-1,3-diaminopropane (boiling point 144° C.);
(C-6) triethylamine (boiling point 89° C.)
C-20 octylamine (boiling point 176° C.);
C-21 monoethanolamine (boiling point 174° C.);
C-22 hydroxylamine (boiling point 58° C.);
C-23 tetramethylammonium hydroxide aqueous solution (20%) (boiling point 102° C.)
C-24 dipropylamine
C-25 N-methylbutylamine (Test Example 1) Polymer Removability Evaluation 1—Reticulated Polymer To evaluate the removability for a reticulated polymer, a wafer coated with a cured silicone polymer to a thickness of 80 μm was cut into dices having a size of 2 cm×2 cm, and the dices were used as samples. Solutions of respective compositions according to Examples and Comparative Examples were heat to 25° C. and rotated at 400 rpm. The prepared samples were immersed for 1 minute in the respective composition solutions, washed with isopropyl alcohol (IPA), and dried. Before dipping the samples in the composition solutions, the film thickness of the cured silicone polymer of each sample was measured with a scanning electron microscope (SEM). After dipping, washing, and drying the samples, the thickness of the remaining silicone resin of each sample was measured with a scanning electron microscope (SEM) and the removal rate for each composition solution was calculated and summarized in Tables 3 and 4.

Removal rate (μm/min)=[thickness before test (μm)-thickness after test (μm)]/test time (min)

(Test Example 2) Polymer Removability Evaluation 2—Linear PDMS

To evaluate the removability for linear polydimethylsiloxane (PDMS), a mixture obtained by mixing a prepolymer of polydimethylsiloxane (PDMS) and a curing agent at a predetermined mass ratio was spin-coated on a silicon wafer and cut into dices having a size of 2 cm×2 cm and the dices were used as samples. The composition solutions according to Examples and Comparative Examples were heat to 25° C. and rotated at 400 rpm. The samples were immersed for 1 minute in the respective composition solutions, were washed with IPA, and were dried. After the test, the residue on the surface of each sample was observed with an optical microscope and a SEM. The presence or absence of the residue on each sample was marked in Tables 3 and 4.
o: absence/X: presence (Test Example 3) Metal Corrosion Evaluation 1—Bump Ball To evaluate metal corrosion, a wafer having 1011 bump balls made of Sn, Sn/Ag alloy, or Sn/Au alloy was cut into dices having a size of 2 cm×2 cm and the dices were used as samples. The prepared samples were immersed for 30 minutes in the respective composition solutions according to Examples and Comparative Examples while the composition solutions were heated to 25° C. and rotated at 400 rpm, were washed with IPA, and were dried. The respective samples were observed with a SEM. The number of bump balls that are damaged in each sample was counted and summarized in Tables 3 and 4.

(Test Example 4) Metal Corrosion Evaluation 2—Metal Film

A wafer coated with an aluminum thin film was cut into dices having a size of 2 cm×2 cm, and the dices were used as samples. Solutions of respective compositions according to Examples and Comparative Examples were heat to 25° C. and rotated at 400 rpm. The prepared samples were immersed for 10 minutes in the respective composition solutions, were washed with isopropyl alcohol (IPA), and were dried. After the washing, the thin films on the respective samples were checked with a SEM for defects, and the results are summarized in Tables 3 and 4 according to the criteria described below.
Good: Neither change in surface morphology nor discoloration were observed.
Occurrence Change in surface morphology and discoloration were observed.

TABLE 3

| | Removal rate (μm/min) | Presence/absence of residue | Bump ball damage count (ea/1011) | Al damage |
|---|---|---|---|---|
| Example 1 | 34 | o | 3 | good |
| Example 2 | 30 | o | 4 | good |
| Example 3 | 31 | o | 3 | good |
| Example 4 | 25 | o | 0 | good |
| Example 5 | 24 | o | 1 | good |
| Example 6 | 28 | o | 1 | good |
| Example 7 | 26 | o | 3 | good |
| Example 8 | 25 | o | 0 | good |
| Example 9 | 24 | o | 0 | good |
| Example 10 | 23 | o | 0 | good |
| Example 11 | 46 | o | 3 | good |
| Example 12 | 23 | o | 0 | good |
| Example 13 | 32 | o | 4 | good |
| Example 14 | 48 | o | 4 | good |
| Example 15 | 30 | o | 0 | good |
| Example 16 | 29 | o | 3 | good |
| Example 17 | 31 | o | 0 | good |
| Example 18 | 27 | o | 0 | good |
| Example 19 | 30 | o | 2 | good |
| Example 20 | 30 | o | 23 | good |
| Example 21 | 24 | o | 21 | good |

TABLE 4

| | Removal rate (μm/min) | Presence/absence of residue | Bump ball damage count (ea/1011) | Al damage |
|---|---|---|---|---|
| Comparative Example 1 | 0 | X: | 0 | good |
| Comparative Example 2 | 0 | X: | 0 | good |
| Comparative Example 3 | cannot evaluate | cannot evaluate | cannot evaluate | cannot evaluate |
| Comparative Example 4 | 12 | o | 25 | good |
| Comparative Example 5 | 0 | X: | 675 | occurrence |
| Comparative Example 6 | 0 | X: | 243 | occurrence |
| Comparative Example 7 | 4 | o | 32 | occurrence |
| Comparative Example 8 | 2 | X: | 0 | good |
| Comparative Example 9 | 3 | X: | 0 | good |
| Comparative Example 10 | 8 | X: | 41 | occurrence |
| Comparative Example 11 | 12 | o | 67 | occurrence |
| Comparative Example 12 | 5 | X: | 1011 | occurrence |
| Comparative Example 13 | 18.7 | o | 43 | good |
| Comparative Example 14 | 19 | o | 50 | good |

Referring to Table 3, the polymer removing compositions (Examples 1 to 21) according to the present invention exhibited a high removal rate of 23 μm/min or more for a reticulated silicone-based polymer and an excellent removal performance for a linear silicone-based polymer. In addition, the compositions according to the present invention exhibited a good anti-corrosive effect. When an amine compound having a low boiling point was used (Example 21), or when an amine compound was added in an access amount (Example 20), the performance was slightly lowered but was remarkably superior to those of Comparative Examples.

On the other hand, referring to Table 4, Comparative Examples 7 and 10 to 12 in each of which the amine compound according to the present invention was not used exhibited a removal rate of 12 μm/min or less for a reticulated polymer. That is, the removal rate was remarkably lowered and the corrosion of metal was also remarkably increased in comparison with the cases where the compositions according to Examples were used.

In addition, although the amine compound according to the present invention was used, when water or an alcohol-based compound was used as a solvent (Comparative Examples 5 and 6), it was confirmed that polymer removal was difficult and corrosiveness to a metal was remarkably high. In Comparative Examples 8 and 9 in each of which a protic solvent was used, the polymer removal rate was slow, and residues remained after the polymer removal.

On the other hand, when a polar aprotic solvent was used alone, the polymer was not removed (Comparative Examples 1 and 2). When ammonium fluoride was used as a fluorine compound (Comparative Example 3), a precipitate occurred during the preparation of the composition so that the evaluation cannot be performed. In addition, in Comparative Examples 13 and 14 in which dipropylamine and 'N-methylbutylamine were respectively used as the amine compound, the removal rate for a reticulated polymer was lowered to 20 μm/min or less, and 40 or more bump balls among 1011 bump balls made of Sn, Sn/Ag alloy, or Sn/Au alloy were damaged.

What is claimed is:

1. A composition for removing a polymer, the composition comprising:
    a fluorinated alkyl compound;
    a polar aprotic solvent; and
    an amine compound;
    wherein the composition for removing a polymer does not comprise a compound having a hydroxide (—OH) group;
    wherein the amine compound comprises an acyclic secondary amine compound or an acyclic tertiary amine compound;
    wherein the polar aprotic solvent comprises at least one solvent selected from the group consisting of N,N-diethylacetamide, N,N-dimethylpropanamide, N-methylmorpholine, N-butyl acetate, propylene glycol monomethyl ether acetate, 4-methylpyridine, dimethyl piperazine, triethyl phosphate, and tetraethylurea; and
    wherein the composition contains 0.1 to 20% by weight of the fluorinated alkyl compound, 60 to 99.89% by weight of the polar aprotic solvent, and 0.01 to 20% by weight of the amine compound, with respect to the total weight of the composition.

2. The composition according to claim 1, wherein the amine compound is a compound represented by one of Formulas 1 to 3:

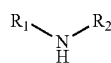

[Formula 1]

In Formula 1, $R_1$ and $R_2$ each independently represent a linear or branched alkyl group having one to eight carbon atoms,

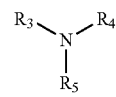

[Formula 2]

In Formula 2, $R_3$ to $R_5$ each independently represent a linear or branched alkyl group having one to eight carbon atoms (C1 to C8),

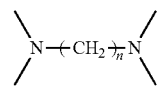

[Formula 3]

In Formula 3, n represents a positive integer among 3, 4, 5, and 6.

3. The composition according to claim 1, wherein the fluorinated alkyl compound comprises one or more compounds represented by any one of Formula 4-1 and Formula 4-2:

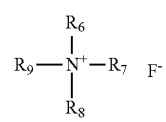

[Formula 4-1]

In Formula 4-1, $R_6$ to $R_9$ each independently represent an alkyl group having three to ten carbon atoms,

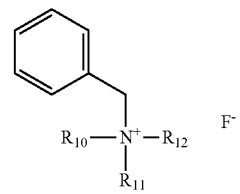

[Formula 4-2]

In Formula 4-2, $R_{10}$ to $R_{12}$ each independently represent an alkyl group having one to ten carbon atoms.

4. The composition according to claim 1, wherein the amine compound comprises at least one compound selected from the group consisting of tripropylamine, tributylamine, tripentylamine, triisobutylamine, dimethyloctylamine, diethylbutylamine, diisobutylamine, N,N,N',N'-tetramethyl-1,3-diaminopropane, N,N,N',N'-tetramethyl-1,4-diaminobutane, and N, N,N',N'-tetramethyl-1,6-diaminohexane.

5. The composition according to claim 1, wherein the amine compound has a boiling point in a range of 140° C. to 300° C.

6. The composition according to claim 1, wherein the composition is used to remove silicone-based polymers.

* * * * *